United States Patent [19]

Atwell et al.

[11] Patent Number: 4,904,659
[45] Date of Patent: Feb. 27, 1990

[54] SUBSTITUTED QUINOLINE DERIVATIVES AND PHARMACEUTICAL COMPOSITIONS THEREOF

[75] Inventors: Graham J. Atwell; Bruce C. Baguley; William A. Denny; Gordon W. Rewcastle, all of Auckland, New Zealand

[73] Assignee: Development Finance Corporation of New Zeland, Wellington, New Zealand

[21] Appl. No.: 266,243

[22] Filed: Oct. 28, 1988

Related U.S. Application Data

[63] Continuation of Ser. No. 877,556, Jun. 23, 1986, abandoned.

[30] Foreign Application Priority Data

Jun. 24, 1985 [NL] Netherlands .................... 212525

[51] Int. Cl.$^4$ .................. C07D 215/48; C07D 403/06; A61K 31/47; A61K 31/535
[52] U.S. Cl. ................... 514/235.2; 514/300; 514/311; 514/314; 514/234.5; 544/128; 546/122; 546/167; 546/169; 546/153
[58] Field of Search ............ 546/169, 167, 153; 514/311, 314

[56] References Cited

U.S. PATENT DOCUMENTS

| | | | |
|---|---|---|---|
| 3,704,322 | 11/1972 | Giannini | 260/558 R |
| 4,567,627 | 1/1984 | Miyano et al. | 514/413 |
| 4,680,299 | 7/1987 | Hesson | 514/311 |

OTHER PUBLICATIONS

Barker, Peter L., "Acylation of Dibasic Compounds Containing Amino Amidine and Aminoguanidine Functions", J. Org. Chem., vol. 46, No. 12, 1981, pp. 2455–2465.

Cain, Bruce F. "Potential Antitumor Agents. 23. 4'-(-9-Acridinylamino) alkanesulfonanilide Congeners Bearing Hydrophilic Functionality", J. Med. Chem. vol. 20, No. 8, 1977, pp. 987–996.

Primary Examiner—David B. Springer
Attorney, Agent, or Firm—Pennie & Edmonds

[57] ABSTRACT

The novel class of substituted quinolines represented by the general formula (I):

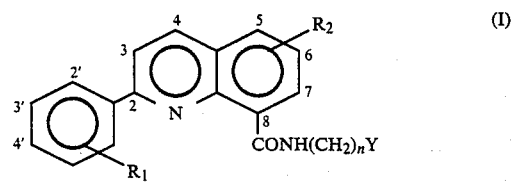

where each of $R_1$ and $R_2$ separately represents H or up to three of the groups lower alkyl, halogen, $CF_3$, CN, $SO_2CH_3$, $NO_2$, OH, $NH_2$, $NHSO_2R_3$, $NHCOOR_3$, $OR_3$, $SR_3$, $NHR_3$ or $NR_3R_3$ (where $R_3$ is lower alkyl optionally substituted with hydroxy, amino or ether functions), and each of $R_1$ and $R_2$ may additionally separately represent the substitution of an aza (—N=) group for one or two of the methine (—CH=) groups in each of the carbocyclic rings, and $R_1$ may also represent, at positions 2', 3' or 4' only, a phenyl ring optionally further substituted with lower alkyl, halogen, $CF_3$, CN, $SO_2CH_3$, $NO_2$, OH, $NH_2$, $NHCOR_3$, $NHCOOR_3$, $OR_3$, $SR_3$, $NHR_3$ or $NR_3R_3$ (where $R_3$ is lower alkyl optionally substituted with hydroxy, amino or ether functions);

Y represents $C(NH)NH_2$, $NHC(NH)NH_2$ or $NR_4R_5$, where each of $R_4$ and $R_5$ is H or lower alkyl optionally substituted with hydroxy, amino or ether functions, or $R_4$ and $R_5$ together with the nitrogen atom form a heterocyclic ring; and n is from 2 to 6;

and the acid addition salts and 1-N-oxides thereof, possess antibacterial and antitumor properties.

5 Claims, No Drawings

SUBSTITUTED QUINOLINE DERIVATIVES AND PHARMACEUTICAL COMPOSITIONS THEREOF

This application is a continuation of U.S. application Ser. No. 877,556, filed June 23, 1986, abandoned, which claimed priority to New Zealand Patent Application No. 212,525, filed on June 24, 1985.

SUMMARY OF THE INVENTION

The present invention relates to novel 2-phenylquinoline derivatives having antitumour and antibacterial activity, to methods of preparing the novel compounds, and to their use as anitbacterial and antitumour agents. The present invention also relates to novel compounds useful as intermediates in the preparation of the 2-phenylquinoline derivatives of the invention.

DESCRIPTION OF THE INVENTION

In one aspect the present invention relates to the novel class of substituted quinolines represented by the general formula (I):

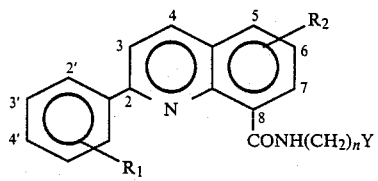
(I)

where each of $R_1$ and $R_2$ separately represents H or up to three of the groups lower alkyl, halogen, $CF_3$, CN, $SO_2CH_3$, $NO_2$, OH, $NH_2$, $NHSO_2R_3$, $NHCOR_3$, $NHCOOR_3$, $OR_3$, $SR_3$, $NHR_3$ or $NR_3R_3$ (where $R_3$ is lower alkyl optionally substituted with hydroxy, amino or ether functions), and each of $R_1$ and $R_2$ may additionally separately represent the substitution of an aza (—N=) group for one or two of the methine (—CH=) groups in each of the carbocyclic rings, and $R_1$ may also represent, at positions 2', 3' or 4' only, a phenyl ring optionally further substituted with lower alkyl, halogen, $CF_3$, CN, $SO_2CH_3$, $NO_2$, OH, $NH_2$, $NHCOR_3$, $NHCOOR_3$, $OR_3$, $SR_3$, $NHR_3$ or $NR_3R_3$ (where $R_3$ is lower alkyl optionally substituted with hydroxy, amino or ether functions);

Y represents $C(NH)NH_2$, $NHC(NH)NH_2$ or $NR_4R_5$, where each of $R_4$ and $R_5$ is H or lower alkyl optionally substituted with hydroxy, amino or ether functions, or $R_4$ or $R_5$ together with the nitrogen atom form a heterocyclic ring; and n is from 2 to 6;

and the acid addition salts and 1-N-oxides thereof.

When $R_1$, $R_2$, $R_3$, $R_4$ or $R_5$ represent lower alkyl, the group may contain from 1 to 5 carbon atoms. Examples of lower alkyl optionally substituted with hydroxy, amino or ether functions include lower alkyl optionally substituted with hydroxy, amino, methylamino, dimethylamino and O-methyl.

A preferred class of compound of the above formula (I) is that where $R_1$ represents one of aza, halogen, $NO_2$, or $OCH_3$, $R_2$ represents H, Y represents $N(CH_3)_2$ and n is 2.

The compounds of formula (I) have antibacterial and antitumour activity, and are useful as antibacterial and antitumour agents.

The compounds of formula (I) form pharmaceutically acceptable addition salts with both organic and inorganic acids. Examples of suitable acids for salt formation are hydrochloric, sulphuric, phosphuric, acetic, citric, oxalic, malonic, salicyclic, malic, fumaric, succinic, ascorbic, maleic, methanesulfonic, and the like.

The compounds of general formula (I) and the acid addition salts and 1-N-oxides thereof may be prepared by a process which comprises coupling a substituted quinoline of the general formula (II):

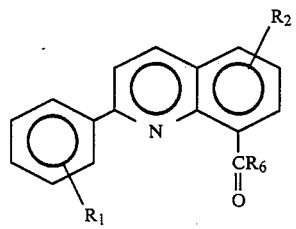
(II)

where $R_1$ and $R_2$ are as defined above and $R_6$ represents Cl, Br, $OC_6H_4$—p—$NO_2$, 0-(1-N-benzotriazole), 1-N-imidazole, or 0-(2-N-methylpyridinium) salts, or the 1-N-oxide thereof, with a primary alkyl amine of the general formula (III):

$$NH_2(CH_2)_nY \qquad (III)$$

where n and Y are as defined above and, if desired, converting a compound of formula (I) into an acid addition salt thereof.

The coupling reaction is desirably performed in an anhydrous solvent (e.g. chloroform, dimethylsulphoxide or N-methylpyrrolidone, but preferably dichloromethane or dimethylformamide) preferably buffered with a tertiary amine (e.g. triethylamine). The reaction is conveniently performed at temperatures in the range of from 0° C. to 50° C., with the preferred temperature being 20° C.

The acid addition salts of the compounds of formula (I) are prepared by contacting the free base form with an equivalent amount of the desired acid in the conventional manner. The free base forms may be regenerated by treating the salt form with a base. For example, dilute aqueous base solutions may be utilized. Dilute aqueous potassium hydroxide, potassium carbonate, ammonia, and sodium bicarbonate solutions are suitable for this purpose. The free base forms differ from their respective salt forms somewhat in certain physical properties such as solubility in polar solvents but the salts are otherwise equivalent to their respective free base forms for the purposes of the invention.

The primary alkyl amines of the general formula (III) are known compounds and are commercially available or preparable by methods described in the literature. Examples of such compounds include N,N-dimethyl-1,2-ethanediamine (N,N-dimethylethylenediamine), N,N-diethyl-1,2-ethanediamine, N,N-dimethyl-1,3-propanediamine, N,N-dimethyl-1,4-butanediamine, N,N-dimethyl-1,5-pentanediamine, N-(2-hydroxyethyl)-1,2-ethanediamine (2-(2-aminoethylamino)ethanol), N-methyl-N-(2-hydroxyethyl)-1,2-ethanediamine, 2-aminoethylguanidine $NH_2(CH_2)_2NHC(NH)CH_2$, and 3-aminopropionamidine $NH_2(CH_2)_2C(NH)NH_2$. The two lastmentioned compounds may be prepared according to P. L. Barker, P. L. Gendler and H. Rapoport, *J. Org. Chem.*, 46, 2455 (1981).

The substituted quinolines of formula (II) are novel compounds useful as intermediates in the preparation of the compounds of formula (I) and accordingly, the present invention also provides the compounds represented by the general formula (II):

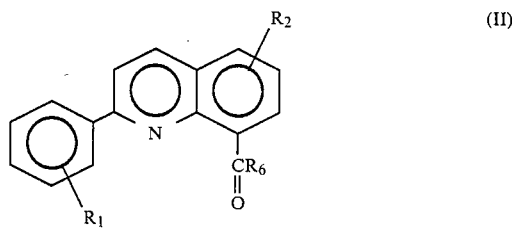

where $R_1$, $R_2$ and $R_6$ are as defined above, and the 1-N-oxides thereof.

Substituted quinoline acids, which are compounds of general formula (II) where $R_6$ is OH, may be prepared by the processes outlined in Scheme I:

$NO_2$ or $OR_3$, where $R_3$ is defined as for formula (I) and $R_1$ and $R_2$ may additionally separately represent the substitution of an aza (—N=) group for one of the methine (—CH=) groups of each of the carbocyclic rings.

Condensation of aromatic aldehydes and o-toluidines together with pyruvic acid (Method I; Doebner reaction) provides 3-methyl-2-phenylquinoline-4-carboxylic acids (VI). An alternative but related preparation of these compounds is via condensation of acetophenones (IV) with 7-methylisatins (V) (Method 2; Pfitzinger reaction). Copper-catalyzed decarboxylation of the acids (VI) provides the methylphenylquinolines (VII), which can also be prepared by condensation of cinnamaldehydes (VIII) with orthotoluidines (IX) (Method 3; Doebner-Miller reactions). Oxidation of the methyl group (using, for example, $SeO_2$ or $H_2SO_4$/$CrO_3$) then gives the desired 2-phenylquinoline-8-carboxylic acids (X) in moderate yields.

Substituted quinoline acids of general formula (II) where $R_6$ is OH may also be prepared by the processes

SCHEME I

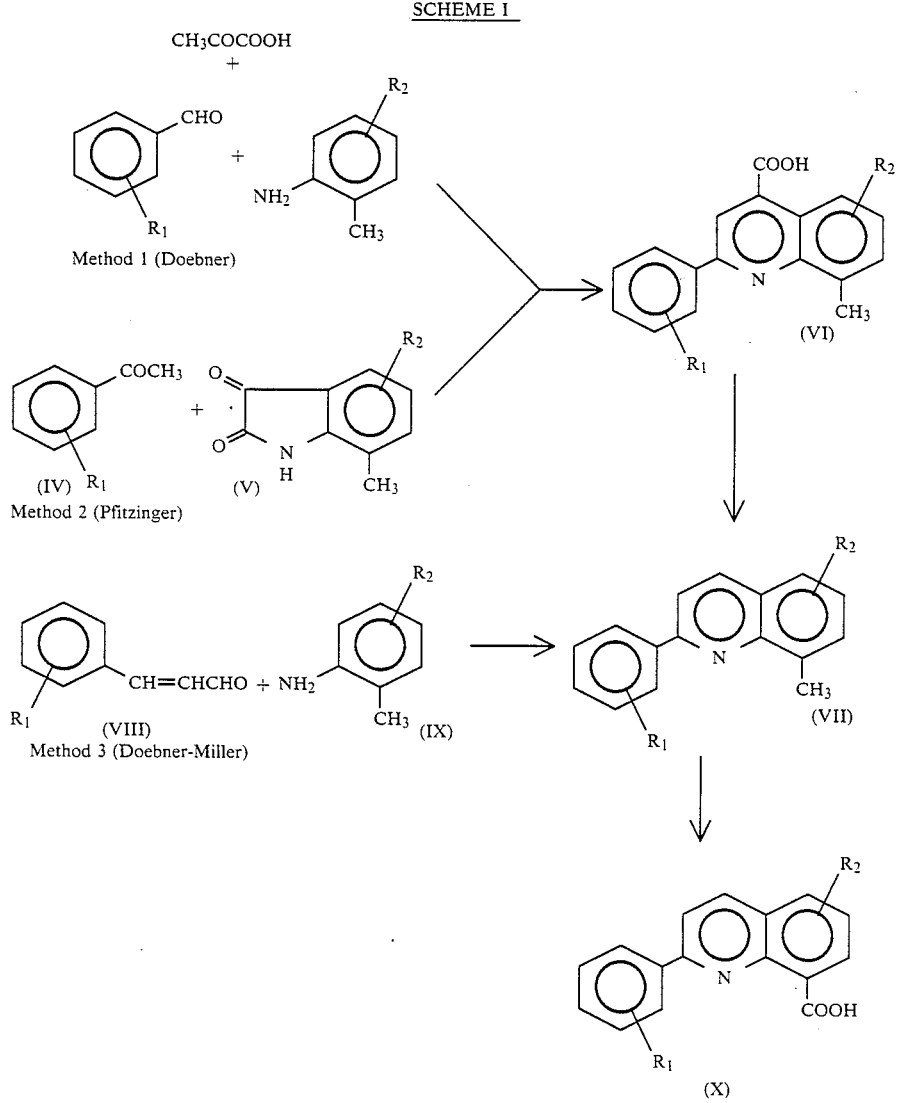

In Scheme I each of $R_1$ and $R_2$ separately represents H or up to two of the groups halogen, $CF_3$, $SO_2CH_3$, outlined in Scheme II:

SCHEME II

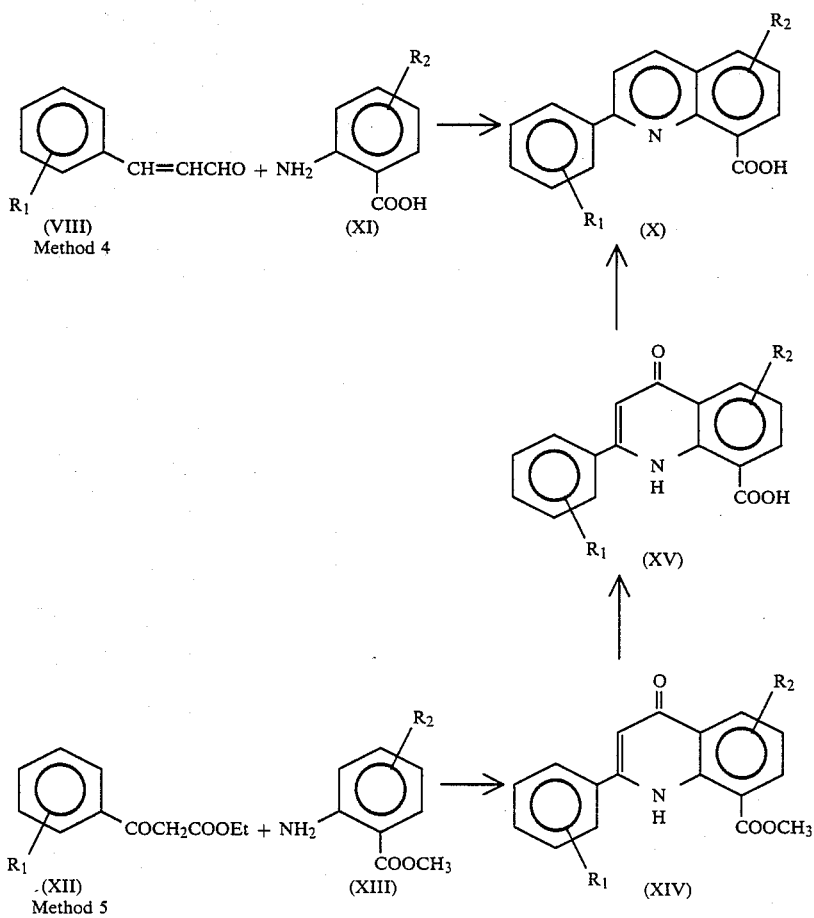

In Scheme II, $R_1$ and $R_2$ are as defined for formula (I).

Direct condensation of cinnamaldehydes (VIII) with anthranilic acids (XI) give the desired acids (X) in low yields (Methods 4). Condensation of benzoylacetates (XII) with methyl anthranilates (XIII) (Method 5) gives good yields of the quinolines (XIV). Hydrolysis to (XV) followed by reduction with Al/Hg amalgam then provides the desired 2-phenylquinoline-8-carboxylic acids (X).

Reaction of the substituted quinoline acids (X) where $R_6$ represents OH (obtained by the methods outlined in Schemes I and II, or by any other method) with a suitable halogen reagent (e.g. $PCl_5$, $POCl_3$, but preferably $SOCl_2$) provides compounds of formula (II) where $R_6$ is Cl. Similar reaction of compounds of general formula (X) with $POBr_3$ or preferably $SOBr_2$ provides compounds of formula (II) where $R_6$ is Br.

Reaction of the substituted quinoline acids (X) with tris(4-nitrophenyl)phosphite in pyridine gives the 4-nitrophenylester derivatives (II) where $R_6$ is $OC_6H_4$—p—$NO_2$ (B. F. Cain, G. J. Atwell and W. A. Denny, J. Med. Chem., 20, 987 (1977)).

Reaction of the substituted quinoline acids (X) with 1,1'-carbonyldiimidazole in DMF or N-methylpyrrolidone gives the imidazolide derivatives of formula (II) where $R_6$ is 1-N-imidazole, i.e.

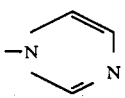

Reaction of the substituted quinoline acids (X) with 2-chloro-N-methylpyridinium salts in DMF or N-methyl-pyrrolidone gives the 2N-methylpyridinium salt esters of formula (II) where $R_6$ is an 0-(2-N-methylpyridinium) salt, i.e.

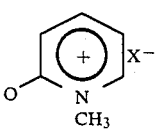

Reaction of the substituted quinoline acids (X) with bis(1-N-benzotriazole)carbonate in DMF or N-methylpyrrolidone gives the 1-N-benzotriazole esters of formula (II) where $R_6$ is 0-(1-N-benzotriazole), i.e.

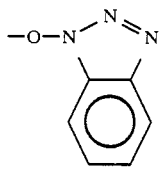

The compounds of general formula (II) where $R_6$ is as defined above are then coupled wih suitable primary amines of formula (III) as described above to provide compounds of general formula (I).

The 1-N-oxides of the compounds of formula (I) may be prepared by the process outlined in Scheme III:

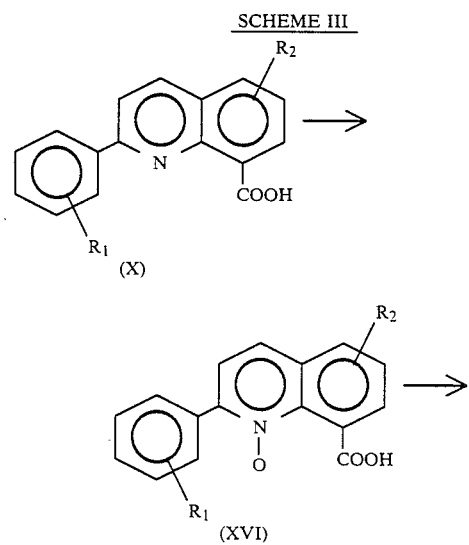

SCHEME III

-continued
SCHEME III

In Scheme III, $R_1$, $R_2$, Y and n are as defined above for formula (I).

Oxidation of the substituted quinoline acids (X) with metachloroperbenzoic acid in chloroform or $H_2O_2$ in acetic acid provides the 1-N-oxide derivatives (XVI) which can be elaborated by the previously described methods to the desired products (XVII).

The following Tables I and II set out physical data for 26 compounds within the general formula (I), representative of it, and preparable by the processes of the invention. In Table I the following terms and abbreviations are used:

Mp-melting point of the reported acid addition salt in °C.,

Rm-a measure of the compound's liphophilic-hydrophilic balance from reversed phase partition chromatography. Rm is linearly related to partition coefficients obtained in the 1-octanol/water system.

TABLE I

| No. | $R_1$ | $R_2$ | n | Y | Mp (°C.) | Rm |
|---|---|---|---|---|---|---|
| 1 | H | H | 2 | $N(CH_3)_2$ | 114–116 | −0.01 |
| 2 | H | H | 3 | $N(CH_3)_2$ | 214–216 | 0.06 |
| 3 | H | H | 4 | $N(CH_3)_2$ | 208–209 | 0.14 |
| 4 | H | H | 5 | $N(CH_3)_2$ | 171–174 | 0.21 |
| 5 | H | H | 2 | $NH(CH_2)_2OH$ | 190–193 | |
| 6 | H | H | 2 | NH Morpholide | 206–209 | |
| 7 | 2'-aza | H | 2 | $N(CH_3)_2$ | 168–170 | −1.43 |
| 8 | 2'-Cl | H | 2 | $N(CH_3)_2$ | 169–171 | 0.15 |
| 9 | 3'-aza | H | 2 | $N(CH_3)_2$ | 249–252 | −0.58 |
| 10 | 3'-Cl | H | 2 | $N(CH_3)_2$ | 110–111 | 0.05 |
| 11 | 3'-$OCH_3$ | H | 2 | $N(CH_3)_2$ | 118–120 | |
| 12 | 4'-aza | H | 2 | $N(CH_3)_2$ | 235–237 | −0.87 |
| 13 | 4'-F | H | 2 | $N(CH_3)_2$ | 133–136 | |
| 14 | 4'-Cl | H | 2 | $N(CH_3)_2$ | 250–251 | 0.05 |
| 15 | 4'-Br | H | 2 | $N(CH_3)_2$ | 123–124 | |
| 16 | 4'-I | H | 2 | $N(CH_3)_2$ | 118–119 | |
| 17 | 4'-Ph | H | 2 | $N(CH_3)_2$ | 180–183 | |
| 18 | 4'-$OCH_3$ | H | 2 | $N(CH_3)_2$ | 200–201 | −0.16 |
| 19 | 4'-OH | H | 2 | $N(CH_3)_2$ | 270–273 | −0.33 |
| 20 | 4'-$NO_2$ | H | 2 | $N(CH_3)_2$ | 244–245 | −0.18 |
| 21 | 4'-$NH_2$ | H | 2 | $N(CH_3)_2$ | 116–120 | −0.76 |
| 22 | 4'-$NHCOCH_3$ | H | 2 | $N(CH_3)_2$ | 160–164 | |
| 23 | 4'-$NHSO_2CH_3$ | H | 2 | $N(CH_3)_2$ | 274–275 | −0.38 |
| 24 | H | 4-aza | 2 | $N(CH_3)_2$ | 229–231 | |
| 25 | H | 5-Cl | 2 | $N(CH_3)_2$ | 245–246 | |
| 26 | H | 6-$NO_2$ | 2 | $N(CH_3)_2$ | 280–282 | |

TABLE II

| | | ELEMENTAL ANALYSES FOR THE COMPOUNDS OF TABLE I | | | | | | | |
| | | | Found | | | | Calculated | | |
| No | Formula | MW | C | H | N | Cl | C | H | N | Cl |
| 1 | $C_{20}H_{21}N_3O.2HCl$ | 392.3 | 61.5 | 6.0 | 10.7 | 17.9 | 61.2 | 5.9 | 10.7 | 18.1 |

TABLE II-continued
ELEMENTAL ANALYSES FOR THE COMPOUNDS OF TABLE I

| No | Formula | MW | Found C | Found H | Found N | Found Cl | Calculated C | Calculated H | Calculated N | Calculated Cl |
|---|---|---|---|---|---|---|---|---|---|---|
| 2 | $C_{21}H_{23}N_3O.2HCl$ | 406.3 | 62.7 | 6.6 | 10.4 | | 62.1 | 6.2 | 10.3 | |
| 3 | $C_{22}H_{25}N_3O.HCl$ | 383.92 | 68.9 | 6.5 | 10.8 | 9.4 | 68.8 | 6.8 | 10.9 | 9.2 |
| 4 | $C_{23}H_{27}N_3O.HCl$ | 397.94 | 69.1 | 7.0 | 10.5 | 9.2 | 69.4 | 7.1 | 10.6 | 8.9 |
| 5 | $C_{20}H_{21}N_3O_2.2HCl$ | 408.33 | 58.7 | 5.5 | 10.2 | 17.2 | 58.8 | 5.7 | 10.3 | 17.4 |
| 6 | $C_{22}H_{23}N_3O_2.2HCl$ | 434.37 | 60.5 | 5.9 | 9.9 | | 60.8 | 5.8 | 9.7 | |
| 7 | $C_{19}H_{20}N_4O.2HCl$ | 393.32 | 58.1 | 5.5 | 14.1 | 17.9 | 58.0 | 5.6 | 14.2 | 18.0 |
| 8 | $C_{20}H_{20}ClN_3O.HCl$ | 390.31 | 61.4 | 5.4 | 10.7 | | 61.5 | 5.4 | 10.8 | |
| 9 | $C_{19}H_{20}N_4O.2HCl$ | 393.32 | 58.1 | 5.9 | 14.4 | 18.3 | 58.0 | 5.6 | 14.2 | 18.0 |
| 10 | $C_{20}H_{20}ClN_3O$ | 353.85 | 68.1 | 5.5 | 11.9 | 10.0 | 67.9 | 5.7 | 11.9 | 10.0 |
| 11 | $C_{21}H_{23}N_3O_2.2HCl.H_2O$ | 440.38 | 57.0 | 6.3 | 9.5 | 16.0 | 57.3 | 6.2 | 9.5 | 16.1 |
| 12 | $C_{19}H_{20}N_4O.2HCl$ | 393.32 | 58.0 | 5.6 | 14.2 | 18.0 | 58.0 | 5.6 | 14.2 | 18.0 |
| 13 | $C_{20}H_{20}FN_3O.2HCl$ | 410.33 | 58.4 | 5.4 | 10.1 | 18.0 | 58.5 | 5.4 | 10.2 | 17.3 |
| 14 | $C_{20}H_{20}ClN_3O.HCl$ | 390.31 | 61.4 | 5.3 | 10.9 | | 61.5 | 5.4 | 10.8 | |
| 15 | $C_{20}H_{20}BrN_3O$ | 398.35 | 60.4 | 4.9 | 10.6 | | 60.3 | 5.1 | 10.6 | |
| 16 | $C_{20}H_{20}N_3OI$ | 445.29 | 54.0 | 4.3 | 9.2 | | 53.9 | 4.5 | 9.4 | |
| 17 | $C_{26}H_{25}N_3O.2HCl$ | 468.43 | 66.9 | 6.0 | 8.9 | 15.2 | 66.7 | 5.8 | 9.0 | 15.1 |
| 18 | $C_{21}H_{23}N_3O_2.2HCl$ | 422.36 | 59.8 | 6.3 | 10.3 | 16.8 | 59.7 | 6.0 | 10.0 | 16.8 |
| 19 | $C_{20}H_{21}N_3O_2.2HBr$ | 497.33 | 48.0 | 4.5 | 8.8 | 31.9(Br) | 48.3 | 4.7 | 8.5 | 32.2(Br) |
| 20 | $C_{20}H_{20}N_4O_3.HCl$ | 400.87 | 60.2 | 5.6 | 13.9 | 9.0 | 59.9 | 5.3 | 14.0 | 8.9 |
| 21 | $C_{20}H_{22}N_4O.2HCl$ | 407.35 | 58.7 | 4.6 | 13.2 | | 59.0 | 5.9 | 13.7 | |
| 22 | $C_{22}H_{24}N_4O_2.2HCl$ | 449.39 | 59.1 | 6.1 | 12.5 | 15.9 | 58.8 | 5.8 | 12.5 | 15.8 |
| 23 | $C_{21}H_{24}N_4O_3S.2HCl$ | 486.24 | 51.8 | 5.4 | 11.2 | 14.9 | 52.0 | 5.4 | 11.5 | 14.6 |
| 24 | $C_{19}H_{19}N_4O.HCl$ | 356.8 | 63.7 | 6.1 | 15.6 | 10.0 | 63.9 | 5.9 | 15.7 | 9.9 |
| 25 | $C_{20}H_{20}ClN_3O.HCl$ | 390.32 | 61.4 | 5.4 | 10.7 | 18.2 | 61.5 | 5.4 | 10.8 | 18.2 |
| 26 | $C_{20}H_{20}N_4O_3.HCl$ | 400.87 | 59.9 | 5.4 | 14.1 | 9.1 | 60.0 | 5.3 | 14.0 | 8.8 |

The following Examples illustrate the preparation of compounds represented by the general formula (I)

EXAMPLE A

Preparation of Compound 1 of Table I by Method 1 of Scheme I

8-Methyl-2-phenylquinoline-4-carboxylic acid (VI; $R_1=R_2=H$)

A solution of 2-methylaniline (28 g) in EtOH (50 mL) was added to a solution of pyruvic acid (33 g) and benzaldehyde (28 g) in EtOH (100 mL), and the mixture was heated under reflux for 3 h and then allowed to cool overnight. The resulting solid was collected by filtration, washed well with cold EtOH and benzene and dried to give a product (13.4 g) of acceptable purity. A sample crystallized from EtOH had mp 245°–246° C. (lit. mp 245° C. Doebner and Giesecke, Ann. 1887, 242, 290).

8-Methyl-2-phenylquinoline (VII; $R_1=R_2=H$)

The above acid (9 g) and Cu powder (0.7 g) were heated at 280°–290° C. until cessation of gas evolution. The cooled melt was extracted with boiling petroleum ether (bp 40°–60° C.) in the presence of charcoal, and the resulting solution was filtered and concentrated to give the crude product (7 g) suitable for the next step. A sample was crystallized from petroleum ether as plates, mp 49°–50° C.

2-Phenylquinoline-8-carboxylic acid (X; $R_1=R_2=H$)

The above methylquinoline (5 g) and $SeO_2$ (5.5 g) were mixed and heated to 180°–190° C., when an exothermic reaction occurred which raised the internal temperature to 270°–280° C. The mixture was held at this temperature for 2 min, cooled, and the melt was extracted with hot $CHCl_3$. The resulting oil from this extraction was extracted with boiling dilute KOH and clarified by filtration. Excess AcOH then precipitated the crude acid, which was crystallized from EtOH to give the pure compound, mp 159°–161° C. (Elderfield, R. C., Gensler, W. J., Brembry, T. H., Williamson T. A. and Weisl, H., J. Am. Chem. Soc., 1946, 68, 1589 record mp 158°–159° C.).

Compound 1 of Table I

The above acid (1 equivalent) was suspended in dry DMF (10 mL/g) and treated with 1,1'-carbonyldiimidazole (1.5 equivalents) at 20°–40° C. for 1 h. The homogeneous mixture was cooled to 5° C., treated with N,N-dimethylethylenediamine (2.5 equivalents), kept at 20° C. for 15 min and then most of the solvent was removed under reduced pressure. Addition of dilute aqueous $Na_2CO_3$ precipitated a solid which was extracted with $CH_2Cl_2$. The dried organic layer was evaporated and the residue of pure base was crystallized from MeOH—EtOAc—HCl to give the dihydrochloride, mp 114°–116° C. Anal. ($C_{20}H_{21}N_3O.2HCl$) C,H,N,Cl.

Compounds 2 to 6 of Table I were similarly prepared from 2-phenylquinoline-8-carboxylic acid by substitution of the appropriate amine in the above procedure.

EXAMPLE B

Preparation of Compound 7 of Table I by Method 2 of Scheme I

8-Methyl-2-(2-pyridyl)quinoline-4-carboxylic acid (VI; $R_1=2'$-aza, $R_2=H$)

A mixture of 2-acetylpyridine (IV; $R_1=2$-aza: 6.05 g, 0.05 mol) and 7-methylisatin (V; $R_2=H$: 8.52 g, 0.053 mol) in 65 mL of 50% EtOH—$H_2O$ containing KOH (13 g) was refluxed for 2 h, then diluted with 50% EtOH—$H_2O$ to obtain a homogeneous solution, filtered and acidified (HOAc). The resulting acid was collected, washed with 30% EtOH—$H_2O$ and recrystallized from DMF—EtOH to provide the product (9.4 g, 67%, mp. 319°–320° C. Anal. ($C_{16}H_{12}N_2O_2$) C,H,N.

Similar reactions using appropriately substituted acetophenones gave the 8-methyl-2-phenylquinoline-4-carboxylic acids (VI) listed in Table III.

8-Methyl-2-(2-pyridyl)quinoline (VII; $R_1=2'$-aza, $R_2=H$)

The preceding quinoline acid (V; $R_1=2'$-aza, $R_2=H$; 7.0 g) and Cu powder (0.5 g) were heated at 280°–290° C. until cessation of gas evolution. The cooled melt was extracted with boiling petroleum ether (bp 40°–60° C.) in presence of charcoal and the filtered solution evaporated to provide the crude product (5.2 g). A sample crystallized from petroleum ether (bp 40°–60° C.) as plates, mp. 83°–84° C. Anal. ($C_{15}H_{12}N_2$) C,H,N.

Similar decarboxylations of the quinoline acids (VI) listed in Table III gave the 8-methyl-12-phenyl-quinolines (VII) listed in Table IV.

2-(2-pyridyl)quinoline-8-carboxylic acid (X; $R_1=2'$-aza, $R_2=H$)

The above methylquinoline (VII; $R_1=2'$-aza, $R_2=H$: 3.5 g) and $SeO_2$ (4.2 g) were heated with mixing to 180°–190° C., when a violent exothermic reaction occurred and the temperature rose rapidly to 270°–280° C. The reaction mixture was held at this temperature for 2 min, then cooled and the melt extracted with hot $CHCl_3$. Evaporation left an oil which was extracted with boiling dilute aq.KOH (charcoal), clarified by filtration, partially neutralised with HOAc, and refiltered. Excess HOAc, was then added to precipitate the crude product. Crystallization of this material from benzene-petroleum ether and then EtOH afforded the pure quinoline acid (X) (1.44 g, 36%) as needles, mp. 199°–201° C. Anal: ($C_{15}H_{10}N_2O_2$) C,H,N.

Similar oxidations of the methylquinolines (VII) listed in Table IV gave the 2-phenylquinoline-8-carboxylic acids (X) listed in Table V.

Compound 7 of Table I

The above acid (X; $R_1=2'$-aza, $R_2=H$) was treated with 1,1'-carbonyldiimidazole and N,N-dimethylethylenediamine as described in Example A to give compound 7 as needles, mp 168°–170° C. Anal. ($C_{19}H_{20}N_4.2HCl$) C,H,N,Cl.

Compounds 8 to 18 and 25 to 26 of Table I were similarly prepared from the 2-phenylquinoline-8-carboxylic acids (X) listed in Table V.

TABLE III

8-METHYL-2-PHENYLQUINOLINE-4-CARBOXYLIC ACIDS (VI)

| $R_1$ | $R_2$ | Mp (°C.) | Formula | Analyses |
|---|---|---|---|---|
| 2'-Cl | H | 230–231 | $C_{17}H_{12}ClNO_2$ | C,H,N |
| 3'-aza | H | 250–252 | $C_{16}H_{12}N_2O_2.\tfrac{1}{2}H_2O$ | C,H,N |
| 3'-Cl | H | 272–274 | $C_{17}H_{12}ClNO_2$ | C,H,N,Cl |
| 3'-OCH$_3$ | H | 210–211 | $C_{18}H_{15}NO_3$ | C,H,N |
| 4'-aza | H | 347–349 | $C_{16}H_{12}N_2O_2$ | C,H,N |
| 4'-F | H | 249–251 | $C_{17}H_{12}FNO_2$ | C,H,N,F |
| 4'-Cl | H | 253–255 | $C_{17}H_{12}ClNO_2$ | C,H,N |
| 4'-Br | H | 256–257 | $C_{17}H_{12}BrNO_2$ | C,H,N,Br |
| 4'-I | H | 276–278 | $C_{17}H_{12}INO_2$ | C,H,N,I |
| 4'-Ph | H | 237–239 | $C_{23}H_{17}NO_2$ | C,H,N |
| 4'-OCH$_3$ | H | 242–244 | $C_{17}H_{15}NO_3$ | C,H,N |
| H | 5-Cl | 287–289 | $C_{27}H_{12}ClNO_2$ | C,H,N,Cl |
| H | 6-NO$_2$ | 185–186 | $C_{17}H_{12}N_2O_4$ | C,H,N. |

TABLE IV

8-METHYL-2-PHENYLQUINOLINES (VII)

| $R_1$ | $R_2$ | Mp (°C.) | Formula | Analysis |
|---|---|---|---|---|
| 2'-Cl | H | 89–91 | $C_{16}H_{12}ClN$ | C,H,N,Cl |
| 3'-aza | H | 54–55 | $C_{15}H_{12}N_2$ | C,H,N |
| 3'-Cl | H | 58–60 | $C_{16}H_{12}ClN$ | C,H,N |
| 3'-OCH$_3$ | H | 67.5–68 | $C_{17}H_{15}NO$ | C,H,N |
| 4'-aza | H | 77–78 | $C_{15}H_{12}N_2$ | C,H,N |
| 4'-F | H | 70–72 | $C_{15}H_{12}FN$ | C,H,N |
| 4'-Cl | H | 78–78.5 | $C_{16}H_{12}ClN$ | C,H,N,Cl |
| 4'-Br | H | 84–85 | $C_{16}H_{12}BrN$ | C,H,N,Br |
| 4'-I | H | 102–103 | $C_{16}H_{12}IN$ | C,H,N |
| 4'-Ph | H | 178–180 | $C_{22}H_{17}N$ | C,H,N |
| 4'-OCH$_3$ | H | 85–85.5 | $C_{17}H_{15}N$ | C,H,N |
| H | 5-Cl | 97–98 | $C_{16}H_{12}ClN$ | C,H,N,Cl |
| H | 6-NO$_2$ | 171–171.5 | $C_{16}H_{12}N_2O_2$ | C,H,N,Cl |

TABLE V

2-PHENYLQUINOLINE-8-CARBOXYLIC ACIDS (X)

| $R_1$ | $R_2$ | Mp (°C.) | Formula | Analysis |
|---|---|---|---|---|
| 2'-Cl | H | 251–252 | $C_{16}H_{10}ClNO_2$ | C,H,N,Cl |
| 3'-aza | H | 224–226 | $C_{15}H_{10}N_2O_2$ | C,H,N |
| 3'-Cl | H | 233–236 | $C_{16}H_{10}ClNO_2$ | C,H,N,Cl |
| 3'-OCH$_3$ | H | 137–138 | $C_{17}H_{13}NO_3$ | C,H,N |
| 4'-aza | H | 255–257 | $C_{15}H_{10}N_2O_2$ | C,H,N |
| 4'-F | H | 214–215 | $C_{16}H_{10}FNO_2$ | C,H,N,F |
| 4'-Cl | H | 209–210 | $C_{16}H_{10}ClNO_2$ | C,H,N,Cl |
| 4'-Br | H | 226–227 | $C_{16}H_{10}BrNO_2$ | C,H,N,Br |
| 4'-I | H | 236–238 | $C_{16}H_{10}INO_2$ | C,H,N |
| 4'-Ph | H | 200–201 | $C_{22}H_{15}NO_2$ | C,H,N |
| 4'-OCH$_3$ | H | 172–173 | $C_{17}H_{13}NO_3$ | C,H,N |
| H | 5-Cl | 241–242 | $C_{18}H_{10}ClNO_2$ | C,H,N,Cl |
| H | 6-NO$_2$ | 268–269 | $C_{16}H_{10}N_2O_4$ | C,H,N |

EXAMPLE C

Preparation of Compound 20 of Table I by Method 3 of Scheme I

8-Methyl-2-(4-nitrophenyl)quinoline (VII: $R_1=4'$-NO$_2$, $R_2=H$)

A mixture of 4-nitrocinnamaldehyde (VIII: $R_1=4'$-NO$_2$) (71 g, 0.40 mol), 2-methylaniline (IX: $R_2=H$ (48 g, 0.45 mol) and conc. HCl (150 mL) was stirred and heated in an oil bath at 140°–150° C. for 5 h. The hot acidic solution was decanted, and the remaining tar was extracted with hot conc. HCl (150 mL). The combined acid fractions were concentrated under reduced pressure and basified with ammonia and the resulting oil was extracted with $CHCl_3$. The crude product from evaporation of the $CHCl_3$ was crystallized, first as the methanesulfonate salt from boiling aqueous methanesulfonic acid, and then as the free base from petroleum ether (bp 100°–120° C.) and finally from EtOAc to give pure product as pale yellow needles (8.1 g), mp 117°–117.5° C. Anal. ($C_{16}H_{12}N_2O_2$) C,H,N.

This is a modification of the literature procedure for the preparation of 2-(4-nitrophenyl)quinoline.

2-(4-Nitrophenyl)quinoline-8-carboxylic acid (X: $R_1=4'$-NO$_2$, $R_2=H$)

A stirred solution of the above methylquinoline (2.3 g) in conc. $H_2SO_4$ (25 mL) and water (40 mL) was heated to 90° C. and treated portionwise with $CrO_3$ (9.9 g) at such a rate as to maintain the temperature below 105° C. After completion of the reaction the mixture was diluted with water, and the resulting precipitate was collected, washed with water, dissolved in hot dilute aqueous KOH, and filtered. Slow addition of dilute aqueous AcOH precipitated impurities which were removed by filtration. Addition of excess AcOH then provided the required product. Two recrystallizations from AcOH/MeOH afforded the pure acid as pale yellow needles (64% yield), mp 272°–274° C. Anal. ($C_{16}H_{10}N_2O_4$) C,H,N.

Compound 20 of Table I

The above acid was treated with 1,1'-carbonyldiimidazole and N,N-dimethylethylenediamine as described in Example A to give compound 20 as the monohydrochloride, mp 244°–245° C. Anal. ($C_{20}H_{20}N_4O_3HCl$) C,H,N,Cl.

EXAMPLE D

Preparation of Compound 1 of Table I by Method 4 of Scheme II

2-Phenylquinoline-8-carboxylic Acid (X; $R_1=R_2=H$)

A mixture of conc. $H_2SO_4$ (45 mL), water (5 mL), AcOH (5 mL), anthranilic acid (XI; $R_2=H$) (20.5 g) and $H_3AsO_4$ (80% w/w; 32 g) was heated with stirring to 105° C., and then treated with cinnamaldehyde (VIII; $R_1=H$) (25 g) at the rate which maintained the temperature at 105°–110° C. The reaction mixture was stirred for a further 3 h at 110°–115° C., then cooled and strongly basified with aqueous KOH. The aqueous layer was decanted from a quantity of tar, washed with $CHCl_3$ and then acidified with AcOH. The resulting precipitate was chromatographed on $SiO_2$ and eluted with a gradient of MeOH in $CH_2Cl_2$ to give a low yield of the desired acid, mp 160°–161° C., identical in all respects to the compound obtained in Example A. This compound was elaborated to compound 1 of Table I by the method outlined in Example A.

EXAMPLE E

Preparation of Compound 1 of Table I by Method 5 of Scheme II

8-Methoxycarbonyl-2-phenyl-4(1H)-quinolone (XIV; $R_1=R_2=H$)

A mixture of methyl anthranilate (XIII; $R_2=H$: 75.6 g, 0.50 mol) and ethyl benzoylacetate (XII; $R_1=H$: 96 g, 0.50 mol) in benzene (400 mL) containing methanesulfonic acid (0.5 ml) was refluxed for 36 h under a Dean-Stark water entrainment head. After concentration to half volume, petroleum ether was added to precipitate a white solid (64 g) that was collected and added over a 15 min period to refluxing Dowtherm A (255° C.) The cooled mixture was diluted with benzene-petroleum ether and the resulting solid was collected, washed with benzene-petroleum ether and dried, yielding the crude quinolone (45.8 g). A sample crystallized from benzene as colourless prisms, mp. 216°–217° C. Anal. ($C_{17}H_{13}NO_3$) C, H, N.

2-Phenyl-4(1H)-quinolone-8-carboxylic acid (XV; $R_1=R_2=H$)

A mixture of the above ester (XIV; $R_1=R_2=H$) (40 g) and 500 mL of 50% EtOH—$H_2O$ containing KOH (27 g) was refluxed for 2 h. Enough 30% EtOH—$H_2O$ was added to dissolve the precipitated potassium salt of the product in the hot and then the filtered solution was slowly acidified with HCl—EtOH so as to obtain the quinolone acid in granular form. This material was collected, washed well with 30% EtOH—$H_2O$ and benzene and dried, providing product (34.9 g, 98%) essentially pure by T.L.C. A sample crystallized from DMF—EtOH—$H_2O$ as prisms, mp. 304°–306° C. Anal. ($C_{16}H_{11}NO_3$) C, H, N.

2-Phenylquinoline-8-carboxylic acid (X; $R_1=R_2=H$)

A hot stirred solution of the preceding quinolone acid (XV; $R_1=R_2=H$; 5.5 g) in 300 mL of 50% EtOH—$H_2O$ containing KOH (1.4 g) was treated in portions with aluminium foil that had been pretreated by immersion in a 9% ethanolic solution of $HgCl_2$. Following completion of the reaction the mixture was filtered, acidified (HCl), treated in the hot with $FeCl_3$ (5 g) and refluxed for 30 min. Neutralisation with aq. KOAc precipitated solids that were collected and extracted with hot aq. KOH. Acidification (HOAc) of the filtered extract provided crude product that was recrystallized twice from benzene-petroleum ether providing T.L.C. homogeneous material (15%), mp 159°–161° C. identical to that prepared in Example A.

Compound 1 of Table I

Treatment of the quinoline acid (X; $R_1=R_2=H$) with 1,1'-carbonyldiimidazole and N,N-dimethylethylenediamine by the method described in Example A gave compound 1 of Table I as the dihydrochloride, mp. 114°–116° C.

EXAMPLE F

Preparation of Compound 26 by Method 1 of Scheme I

8-Methyl-6-nitro-2-phenylquinoline-4-carboxylic acid (VI; $R_1=H$, $R_2=6-NO_2$)

Methanesulfonic acid (7.1 mL, 0.11 mol) was stirred into a mixture of 2-methyl-4-nitroaniline (15.2 g, 0.1 mol), benzaldehyde (10.6 g, 0.1 mol) and pyruvic acid (8.8 g, 0.1 mol) and, following an initial exotherm was heated at 100° C. for 3 h. The mixture was cooled and triturated with water and the resulting tar was extracted with hot dilute aqueous $Et_3N$. The solution was treated with charcoal and filtered and the filtrate was acidified with HCl to give the crude product. Two crystallizations from EtOH gave the pure acid as pale yellow prisms (4.6 g, 45% yield), mp 185°–186° C. Anal. ($C_{17}H_{12}N_2O_4$) C, H, N.

This is a modification of a procedure described for the synthesis of 8-nitro-2-phenylquinoline-4-carboxylic acid (Buchman, E. R., McCloskey, C. M., Seneker, J. A. *J. Am. Chem. Soc.*, 1947, 69, 380).

8-Methyl-6-nitro-2-phenylquinoline (VII; $R_1=H$, $R_2=6-NO_2$)

A mixture of the above acid (2 g) and Cu powder (0.2 g) in quinoline (10 mL) was heated to 230° C. for 15 min. The cooled mixture was diluted with water to precipitate the crude product, which was crystallized from MeOH, mp 171°–171.5° C. Anal. ($C_{16}H_{12}N_2O_2$) C, H, N.

6-Nitro-2-phenylquinoline-8-carboxylic acid (X: $R_1=H$, $R_2=6-NO_2$)

The above quinoline was oxidized with $SeO_2$ as described in Example A to give the desired acid, mp 268°–269° C. Anal. ($C_{16}H_{10}N_2O_4$) C, H, N.

Compound 26 of Table 1

The above quinoline acid was treated with 1,1'-carbonyldiimidazole and N,N-dimethylethylenediamine as described in Example A to give compound 26 of Table I, mp 280°–282° C. Anal. ($C_{20}H_{20}N_4O_3.HCl$) C, H, N, Cl.

The compounds of general formula (I), and particularly the Examples listed in Tables I and II, have antitumor activity in both in vitro and in vivo test systems, as shown by the data of Table VI.

The following Table VI gives biological data for the compounds whose physical data has been given in Tables I and II. The abbreviations used in Table VI are:

No—The number given to the corresponding compound in Table I.

$IC_{50}$—The nanomolar concentration of drug which, when added to cultures of L1210 leukemia cells for 70 h, reduces counted cell numbers to 50% of controls. Compounds with $IC_{50}$ values higher than 2000 nanomolar are considered unlikely to show activity in vivo.

OD—The optimal drug dose (in milligrams per kilogram), administered intraperitoneally as a solution in 0.1 ml of 30% v/v ethyl alcohol in water on days 1, 5 and 9 after tumour inoculation. The drug is administered as a soluble acid addition salt.

ILSmax—The percentage increase in lifespan of treated animals over that of control animals injected with tumour alone. The average survival of control mice was 11 days (for P388 leukemia) and 17 days (for Lewis lung carcinoma) ILS values greater than 20% (P388 leukemia) and 40% (Lewis lung carcinoma) are considered statistically significant. Numbers in parentheses after ILS values indicate the number of long-term survivors (out of a group of 6).

Y—Implies a significant value of drug activity at the stated dose.

N—Implies no statistically significant activity.

P388—Is the P388 leukemia.

LL—Is the Lewis lung carcinoma.

Both of these tumour lines were obtained as frozen cell stocks from Mason Research Inc., USA and are passaged intraperitoneally in DBA/25 mice of either sex (P388) or subcutaneously in C57BL/65 mice of either sex (LL) according to the standard methods (*Cancer Chemother. Reports.*, 3, Part 3, p9, 1972).

Groups of six mice (F1 hybrids of DBA/2J male x C57BL/6J female) were injected intraperitoneally (P388) or intravenously (tail vein, LL), with $10^6$ tumour cells on day 0. When given in this manner, P388 cells grow diffusely in the peritoneal cavity, whereas the Lewis lung cells from distinct solid tumour nodules in the lungs. Antitumour activity is determined by published methods (*European J. Cancer*, 19, pp.1607–1613, 1983).

TABLE IV
BIOLOGICAL ACTIVITY OF THE COMPOUNDS OF TABLE I

| No. | In vitro L1210 ($IC_{50}$) | P388 in vivo OD | ILS | Active | LL in vivo OD | ILS | Active |
|---|---|---|---|---|---|---|---|
| 1 | 1300 | 100 | 91 | Y | 100 | 70(4) | Y |
| 2 | 1140 | 100 | 71 | Y | 100 | <40 | N |
| 3 | 680 | 100 | 93 | Y | 100 | 148(2) | Y |
| 4 | 1300 | 150 | <20 | N | 100 | <40 | N |
| 5 |  | 65 | <20 | N |  |  |  |
| 6 |  | 150 | <20 | N |  |  |  |
| 7 | 1640 | 65 | 73(3) | Y | 100 | 91 | Y |
| 8 | 8100 | 100 | <20 | N |  |  |  |
| 9 | 840 | 100 | 58 | Y | 100 | 52(2) | Y |
| 10 | 1200 | 65 | 40 | Y | 100 | <40 | N |
| 11 | 860 | 225 | 46 | Y |  |  |  |
| 12 | 170 | 45 | 145(2) | Y | 65 | 132(3) | Y |
| 13 |  | 100 | <20 | N |  |  |  |
| 14 | 1170 | 100 | 52 | Y | 65 | 91(4) | Y |
| 15 | 600 | 100 | 72 | Y |  |  |  |
| 16 |  | 100 | 48 | Y |  |  |  |
| 17 | 1290 | 100 | <20 | N |  |  |  |
| 18 | 1290 nm | 150 | 42 | Y |  |  |  |
| 19 | 27 | 65 | 22 | Y |  |  |  |
| 20 | 290 | 100 | 71 | Y | 65 | 85 | Y |
| 21 | 200 | 100 | 28 | Y | 100 | 65 | Y |
| 22 | 740 | 65 | <20 | N |  |  |  |
| 23 | 1330 | 65 | <20 | N |  |  |  |
| 24 | 3250 | 150 | 88 | Y |  |  |  |
| 25 |  | 150 | 63 | Y |  |  |  |
| 26 |  | 150 | 63 | Y |  |  |  |

It is clear from the data of Table VI that the 2-phenylquinoline derivatives of general formula (I) include compounds which are active antitumour agents, giving significant levels of life extension when tested against the P388 leukemia or Lewis lung carcinoma systems when given by intraperitoneal or intravenous injection, respectively, and/or significant inhibition of cultured L1210 leukemia cells in vitro. The compounds also show antitumour activity when given by oral and intravenous routes. In addition to high cytotoxicity towards cultured L1210 leukemia cells, they are active in a number of other cultured tumour cell lines, including those originating from human breast and colon tumours. The compounds of general formula (I) are thus indicated for use as antitumour agents.

The compounds also show antibacterial activity; specifically compounds 1 and 12 show in vitro activity against a number of bacterial cell lines. Thus the invention provides for the use of these compounds as antibacterial agents.

The present invention therefore also provides pharmaceutical compositions having antitumour activity and comprising at least one compound of general formula (I) or a pharmaceutically acceptable acid addition salt or 1-N-oxide thereof, and one or more pharmaceutically acceptable carriers or diluents.

The present invention further provides a method for treating tumours and, in particular, cancers in a patient which comprises administering to the patient an antitumour effective amount of at least one compound of formula (I) or a pharmaceutically acceptable addition salt or 1-N-oxide thereof.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 milligrams of active compound.

The tablets, troches, pills, capsules and the like may also contain the following: a binder such as gum tragacenth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically descrete units suitable as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg with, from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

What is claimed is:

1. A compound represented by the general formula (I)

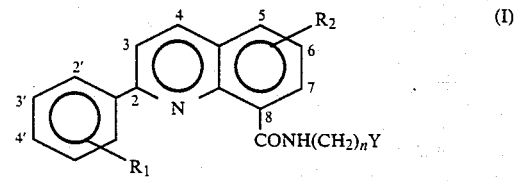

where each of $R_1$ and $R_2$ separately represents H or up to three of the groups lower alkyl, halogen, $CF_3$, CN, $SO_2CH_3$, $NO_2$, OH, $NH_2$, $NHSO_2R_3$, $NHCOR_3$, $NHCOOR_3$, $OR_3$, $SR_3$, $NHR_3$ or $NR_3R_3$ (where $R_3$ is lower alkyl optionally substituted with hydroxy, amino or ether functions), and $R_1$ may additionally represent the substitution of an aza (—N=) group for one of the methine (—CH=) groups in the carbocyclic ring and $R_1$ may also represent, at positions 2', 3' or 4' only, a phenyl ring optionally further substituted with lower alkyl, halogen, $CF_3$, CN, $SO_2CH_3$, $NO_2$, OH, $NH_2$, $NHCOR_3$, $NHCOOR_3$, $OR_3$, $SR_3$, $NHR_3$ or $NR_3R_3$ (where $R_3$ is lower alkyl optionally substituted with hydroxy, amino or ether functions);

Y represents $C(NH)NH_2$, $NHC(NH)NH_2$ or $NR_4R_5$, where each of $R_4$ and $R_5$ is H or lower alkyl optionally substituted with hydroxy, amino or ether functions, or $R_4$ and $R_5$ together with the nitrogen atom form a morpholino ring; and n is from 2 to 6, or an pharmaceutically acceptable acid addition salt or 1-N-oxide thereof.

2. A compound according to claim 1 where $R_1$ and $R_2$ represent H, Y represents $N(CH_3)_2$ and n is 2.

3. A compound according to claim 1 where $R_1$ represents 3'-Cl, $R_2$ represents H, Y represents $N(CH_3)_2$ and n is 2.

4. A compound according to claim 1 where $R_1$ represents 4'-Cl, $R_2$ represents H, Y represents $N(CH_3)_2$ and n is 2.

5. A pharmaceutical composition which comprises at least one compound of the general formula (I) defined in claim 1, or a pharmaceutically acceptable acid addition salt or 1-N-oxide thereof, and one or more pharmaceutically acceptable carriers or diluents.

* * * * *

UNITED STATES PATENT AND TRADEMARK OFFICE
CERTIFICATE OF CORRECTION

PATENT NO. : 4,904,659

DATED : February 27, 1990

INVENTOR(S) : Atwell et al.

It is certified that error appears in the above-identified patent and that said Letters Patent is hereby corrected as shown below:

TITLE PAGE:

Frontispiece [73] "Development Finance Corporation of New Zeland" should read --Development Finance Corporation of New Zealand--;

Abstract, line 5, the compound "$CF_3$, CN, $SO_2CH_3$, $NO_2$, OH, $NH_2$, $NHSO_2R_3$, $NHCOOR_3$, $OR_3$, $SR_3$, $NHR_3$ or $NR_3R_3$" should read --$CF_3$, CN, $SO_2CH_3$, $NO_2$, OH, $NH_2$, $NHSO_2R_3$, $NHCOR_3$, $NHCOOR_3$, $OR_3$, $SR_3$, $NHR_3$ or $NR_3R_3$--

Signed and Sealed this

Twenty-third Day of April, 1991

*Attest:*

HARRY F. MANBECK, JR.

*Attesting Officer*  *Commissioner of Patents and Trademarks*